(12) United States Patent
Beck et al.

(10) Patent No.: US 10,602,914 B2
(45) Date of Patent: Mar. 31, 2020

(54) METHOD FOR TESTING AN OPTICAL INVESTIGATION SYSTEM

(75) Inventors: Gerd Beck, Wurmlingen (DE); Andre Ehrhardt, Wumlingen (DE); Uwe Martin, Spaichingen (DE); Bernhard Gloeggler, Tuttlingen (DE); Hilmar Schachenmayr, Munich (DE); Bryan Kennedy, Santa Barbara, CA (US); Raymond Coussa, Goleta, CA (US); Nathan Tang, Santa Barbara, CA (US)

(73) Assignee: Karl Storz SE & Co. KG, Tuttlingen (DE)

( * ) Notice: Subject to any disclaimer, the term of this patent is extended or adjusted under 35 U.S.C. 154(b) by 340 days.

(21) Appl. No.: 12/969,873

(22) Filed: Dec. 16, 2010

(65) Prior Publication Data

US 2011/0149057 A1 Jun. 23, 2011

(30) Foreign Application Priority Data

Dec. 16, 2009 (DE) .......................... 10 2009 058 662

(51) Int. Cl.
*A61B 1/00* (2006.01)
*A61B 5/00* (2006.01)
(Continued)

(52) U.S. Cl.
CPC .......... *A61B 1/00057* (2013.01); *A61B 1/043* (2013.01); *A61B 5/0059* (2013.01);
(Continued)

(58) Field of Classification Search
CPC .............................. A61B 1/00; A61B 1/00057
See application file for complete search history.

(56) References Cited

U.S. PATENT DOCUMENTS 4,704,520 A * 11/1987 Kanno .................... G01M 11/00
250/205
5,045,704 A * 9/1991 Coates .................... G01N 21/55
250/372

(Continued)

FOREIGN PATENT DOCUMENTS

DE 9320491 U1 8/1994
DE 19638809 A1 4/1998
(Continued)

OTHER PUBLICATIONS

L. Ahlberg, "Can you see me now? Flexible photodetectors could help sharpen photos", University of Wisconsin—Madison News (Jan. 13, 2009).*

(Continued)

*Primary Examiner* — David N Werner
(74) *Attorney, Agent, or Firm* — Whitmyer IP Group LLC

(57) ABSTRACT

A method for testing an optical investigation system, with an imaging device, a video camera and a light source for optical investigation of an object including a reference surface with predetermined optical properties being illuminated with illuminating light from a light source. An image of the reference surface is recorded by the imaging device and the video camera. An operating condition of the video camera that prevails during the recording of the image is recorded. The functionality or another property of the investigation system is determined on the basis of the recorded operating condition.

25 Claims, 5 Drawing Sheets

(51) Int. Cl.
*G01N 21/27* (2006.01)
*A61B 1/04* (2006.01)
*G01N 21/64* (2006.01)
*A61B 5/1495* (2006.01)

(52) U.S. Cl.
CPC ....... *G01N 21/274* (2013.01); *G01N 21/6456* (2013.01); *A61B 5/1495* (2013.01); *A61B 2560/0233* (2013.01); *G01N 21/6447* (2013.01)

(56) References Cited

U.S. PATENT DOCUMENTS

| | | | |
|---|---|---|---|
| 5,053,716 A * | 10/1991 | Hansen et al. | 324/726 |
| 5,111,306 A * | 5/1992 | Kanno | G06F 19/321 |
| | | | 348/74 |
| 5,142,359 A * | 8/1992 | Yamamori | A61B 1/00057 |
| | | | 348/175 |
| 5,674,182 A * | 10/1997 | Suzuki | A61B 1/00057 |
| | | | 600/121 |
| 5,820,547 A * | 10/1998 | Strobl | A61B 1/00057 |
| | | | 348/188 |
| 5,821,523 A * | 10/1998 | Bunte et al. | 235/472.01 |
| 6,361,490 B1 * | 3/2002 | Trion et al. | 600/175 |
| 6,807,876 B2 * | 10/2004 | Beck | A61B 5/0059 |
| | | | 73/865.9 |
| 6,865,962 B2 * | 3/2005 | Gorg et al. | 73/866.5 |
| 8,586,946 B2 * | 11/2013 | Beck et al. | 250/459.1 |
| 2003/0078477 A1 | 4/2003 | Kang et al. | |
| 2003/0105195 A1 | 6/2003 | Holcomb et al. | |
| 2003/0107726 A1 * | 6/2003 | Hirt | G01M 11/33 |
| | | | 356/73.1 |
| 2007/0012885 A1 | 1/2007 | Montagu | |
| 2008/0228031 A1 * | 9/2008 | Leiner | A61B 1/00057 |
| | | | 600/109 |
| 2010/0048993 A1 * | 2/2010 | Shidara | A61B 1/00057 |
| | | | 600/109 |
| 2010/0317919 A1 * | 12/2010 | Takaoka | A61B 1/00057 |
| | | | 600/104 |
| 2011/0149084 A1 * | 6/2011 | Beck et al. | 348/187 |
| 2011/0187842 A1 * | 8/2011 | Yamazaki | A61B 1/00057 |
| | | | 348/68 |
| 2011/0313297 A1 * | 12/2011 | Ishihara | A61B 1/00057 |
| | | | 600/477 |
| 2012/0007001 A1 * | 1/2012 | Ishihara | A61B 1/00057 |
| | | | 250/459.1 |

FOREIGN PATENT DOCUMENTS

| | | |
|---|---|---|
| DE | 19855853 A1 | 6/2000 |
| DE | 10108406 A1 | 8/2001 |
| DE | 112005002223 T5 | 8/2007 |
| EP | 1728464 A1 | 12/2006 |

OTHER PUBLICATIONS

W. Spencer, "Photodetectors", Tech-FAQ (Jun. 30, 2013).*
European Search Report; Application No. EP 10 19 4653; dated Mar. 22, 2011; 6 pages.

* cited by examiner

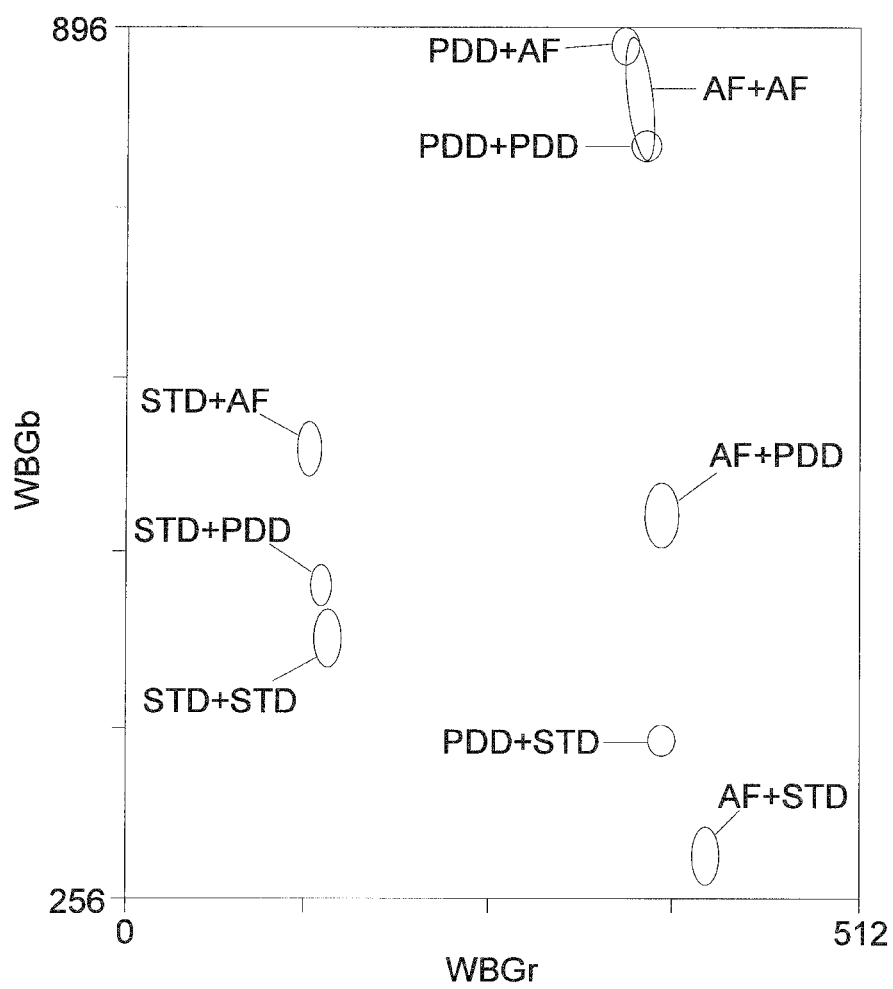

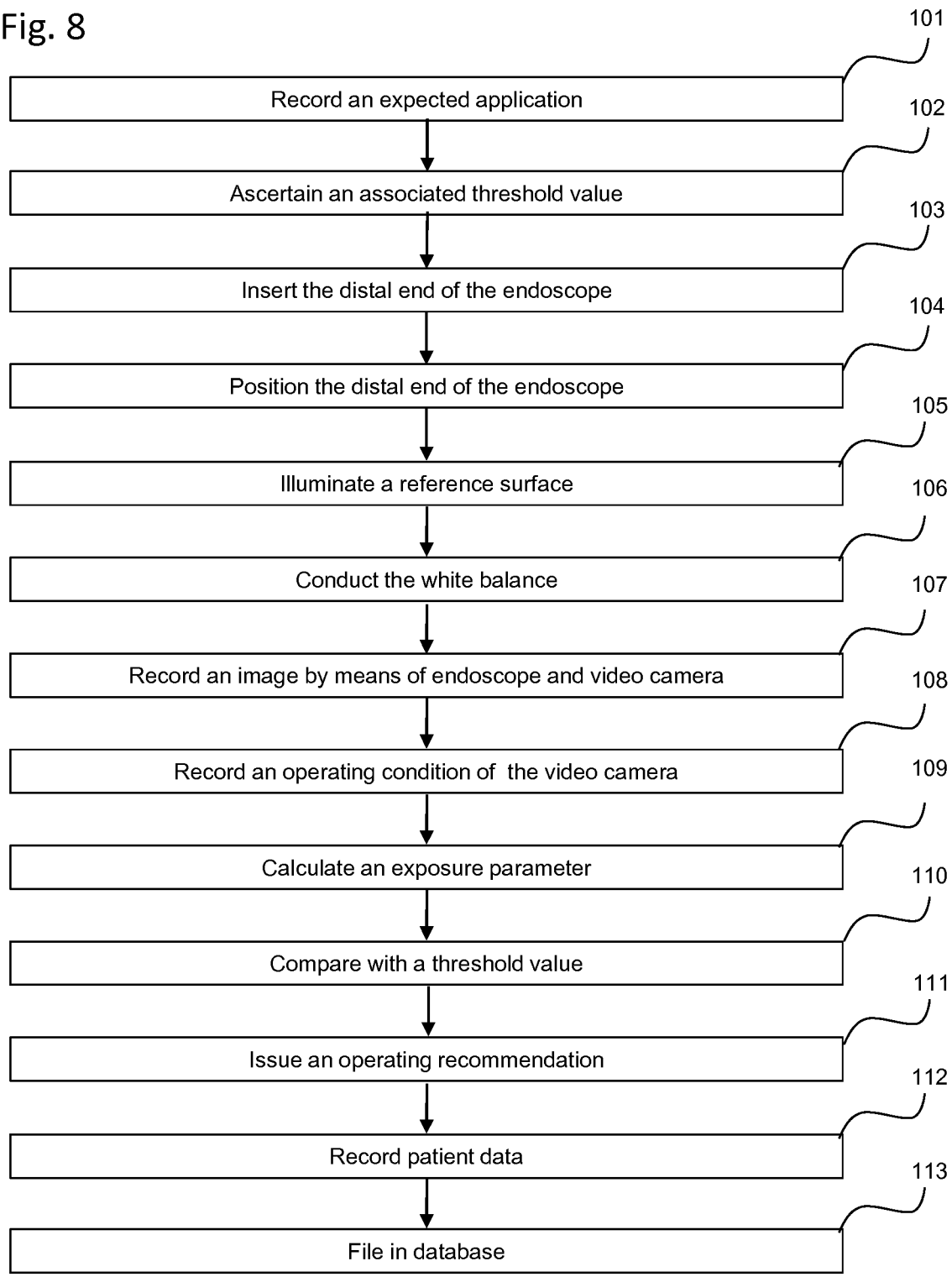

METHOD FOR TESTING AN OPTICAL INVESTIGATION SYSTEM

CROSS-REFERENCE TO RELATED APPLICATIONS

The present application claims priority of German patent application No. 10 2009 058 662.8 filed on Dec. 16, 2009.

FIELD OF THE INVENTION

The present invention relates to a method for testing an optical investigation system, with a light source, an imaging device and a video camera, for optical investigation of an object both within and outside the field of medicine. The present invention relates in particular to a method for testing an endoscopy system with a light source, an endoscope and a video camera

BACKGROUND OF THE INVENTION

Endoscopy systems, consisting of an endoscope and a light source, are used for endoscopy in medical or non-medical applications—in the latter case also known as boroscopy. The light source can be integrated in the endoscope, in particular in its distal end, or can be present as a separate unit, which is optically coupled with an endoscope by a light conductor cable. Light from the light source emerges at the distal end of the endoscope and there illuminates an object to be investigated. Light remitted by the object is captured by a lens on the distal end of the endoscope and conducted onto a light-sensitive image sensor or conveyed, for example by means of an oriented bundle of lightwave conductors or a rod lens system, to the proximal end of the endoscope. In the latter case the light remitted by the object can be observed on the proximal end of the endoscope by an eyepiece or is recorded by means of a video camera. As an alternative or in addition to remitted light, light emitted by the object can also be observed, in particular fluorescent light.

The quality of an image recorded by an endoscopy system, in particular brightness, brightness-color contrast, signal-noise ratio, color fidelity and resolution or sharpness, depends on the observed object, in particular its optical properties, and above all on the endoscopy system. Relevant factors are, for example, the functionality of the light source, its radiant capacity or the light beam generated by it, the spectrum of generated light, in some cases the transmission properties of an employed light conductor cable and the coupling of the light conductor cable with the light source and with the endoscope, the functionality of the light transmission within the endoscope, the degree of effectiveness of the uncoupling of light from the light source out of the endoscope, the functionality or optical properties of the observation beam path in the endoscope, possibly including an oriented bundle of lightwave conductors or a rod lens system, the functionality of the eyepiece or video camera. Frequent sources of failure are, among others, the light source subjected to an alteration process, possibly the light conductor cable and its coupling to the light source and the endoscope, and the coupling of a video camera to the endoscope.

Fluorescent light is observed for medical-diagnostic purposes in particular. In photodynamic diagnostics (PDD), for example, a fluorescence of protoporphyrin IX induced by administered 5-aminolevulinic acid (ALA) is observed. Enrichment of ALA and thus also the intensity of the fluorescence depend on the condition of the tissue. In autofluorescence diagnostics (AF diagnostics) the fluorescence of bodily-produced fluorophores is observed, whose concentration is likewise dependent on the condition of the tissue. Fluorescent diagnostic methods are used in fields other than medicine as well.

To prevent remitted excitation light or illuminating light from outshining the fluorescence, an illumination filter is used in the illumination or excitation beam path between light source and object and in the observation beam path between object and video camera or eyepiece. The illumination filter is a short pass filter, which essentially transmits only the short wavelengths required to excite the fluorescence, but on the other hand primarily or almost exclusively reflects or absorbs longer wavelengths. A very reduced, but not disappearing, transmission in the blocking range is desired with many applications in order to receive, even without fluorescence, an image that has a low brightness but is visible. The observation filter is a long pass filter that transmits only wavelengths of fluorescence and reflects or absorbs short-wave illuminating light remitted by the object. Illumination or excitation filters can as a rule be manually or mechanically exchanged or changed. Observation filters can be replaceable or changeable, but in many cases are firmly built into the endoscope. In urology, for example, for observation in white light, ALA or AF fluorescence, various endoscopes are used that, at least in the observation beam path, are optimized for their respective use or have a corresponding filter characteristic. The aforementioned sources of failure or influences on functionality of the endoscopy system include, in the case of observation of fluorescence, the combination of the illumination filter or spectrum of the light source on the one hand and of the observation filter on the other hand.

A corresponding problem exists with other optical investigation systems, which include an imaging device, a light source and a video camera for optical investigation of medical and non-medical objects in remitted light and/or in fluorescent light. These include exoscopes, which for instance are used for diagnostics and for microsurgical procedures on or close to bodily surfaces.

DE 196 38 809 A1 describes a device for testing and/or adjusting a PDD or PDT (photodynamic therapy) system and/or for training on a system of this type. Positioned in a housing is a target, opposite to which a distal end of an endoscope can be mounted. The curvature of the target can correspond to the variable field curvature of an imaging unit of the endoscope. A photo element and light sources are provided in the target. The photo element records the illuminating strength of an excitation light emitted from the endoscope. A control unit guides the light sources as a function of the illuminating strength recorded by the photo element.

DE 198 55 853 A1 describes an apparatus for testing and/or adjusting a PDD or PDT system and/or for training on a system of this type. The apparatus includes a luminescent phantom with a fluorescent dye. One end of an endoscope can be positioned opposite the luminescent phantom.

In the post-published DE 10 2009 043 696, an apparatus and a method for testing endoscopes are described. The apparatus includes a filter module with several perforations in which optic filters are positioned. The filter module is illuminated from one direction by the light source via a light conductor cable. From an opposite direction the light transmitted by the filter module is observed by means of an endoscope.

Each of the apparatuses and methods known by now, depending on concrete task assignments arising in practice, have advantages and disadvantages. For example, under some conditions and for a few applications none of the described apparatuses and methods allows a reliable testing of a complete endoscopy system or of a different complete optical investigation system in precisely the condition in which it was used or is used medically or non-medically before or afterward.

A disadvantage of the apparatuses and methods described in DE 196 38 809 A1 and in DE 198 55 853 A1 consists in the fact that the video camera automatically post-controls a minor erroneous image brightness, so that it is partially or completely compensated by the camera system and only at very reduced lighting does the image become recognizably poor. Something similar occurs with the human eye. In particular in fluorescent diagnostics, however, the risk of an incorrect diagnosis, in particular the overlooking of a tumor, exists immediately beforehand.

SUMMARY OF THE INVENTION

An object of the present invention consists in providing an improved method for testing an optical investigation system.

This object is fulfilled by the content of the independent claims.

Refinements are indicated in the dependent claims.

Embodiments of the present invention are based on the idea of recording or calling up an operating condition of a video camera of an optical investigation system in the context of a test method and, on the basis of the recorded operating condition, of determining the functionality or another property of the optical investigation system. In many video cameras the operating condition is selected, depending on the existing exposure situation, by the image sensor itself or by a camera control unit (CCU) positioned inside or outside the camera. The operating condition here includes in particular the exposure time as well as the gain factor or other parameters of an analog signal gain in the image sensor. By appropriate algorithms, the exposure time and gain factor, for example, are selected in such a way that the median brightness values of the recorded image (in the form of an existing analog or digital electric signal) or the brightness values of a prioritized area (for example, in the center of the image) of the recorded image assume a predetermined value.

In a light-sensitive image sensor (for example, CCD or CMOS sensor), as a rule, both the exposure time and the analog gain of the electric signals can be selected before their digitization. The longest possible exposure time is thus predetermined by the image repetition frequency. If the image generated by the imaging lens on the image sensor is bright, a short exposure time and a low or minimal gain are selected. With decreasing image brightness, the exposure time is extended, for example, at first at unchanged low gain, to achieve the lowest possible noise. The longest possible exposure time at an image repeating frequency of 50 Hz (50 whole or half images per second) amounts to something less than 20 ms. If the exposure time cannot be further extended, the gain is increased. Thus with decreasing brightness of the image on the image sensor, the noise increases or the signal-noise distance in the signal of the image sensor decreases. When the gain has reached a maximum value with decreasing brightness of the image on the image sensor, only the brightness values of the digitized image can still be numerically scaled. Consequently, with further decreasing brightness the image quality is drastically reduced.

In the described example, with the video camera in operating condition, three stages can be distinguished.

At stage 1 the gain assumes a low, in particular a minimal, value. Alternatively the gain is selected at another predetermined value, for example an average value. Within stage 1 a variation in brightness is compensated by a variation in exposure time. Stage 1 is also designated as auto shutter mode.

In stage 2 the exposure time has the maximum value possible at the given image repetition frequency. Within stage 2 a variation in brightness of the image on the image sensor is compensated by a variation in gain. Stage 2 is also referred to as AGC (auto gain control) mode.

In stage 3 the maximum exposure time and maximum gain are reached. Within stage 3 a variation in brightness of the image on the image sensor has a variation in brightness values of the digital image as a consequence. They can be improved only by a numerical scaling. Here, not only the signal-noise distance decreases, but also the resolution of the brightness values.

For many applications, stage 1 is suited without restriction, while stage 2 is appropriate only with restrictions or up to a certain threshold value of gain and stage 3 is not appropriate. When stage 1 is reached, the optical investigation system is functional without restriction. The radiant power of the light source, possibly the quality of the light conductor cable and its coupling to the light source and endoscope as well as the additional illumination beam path and observation beam path are sufficient in view of the given degree of reflectance of the observed object and its distance from the imaging device.

Within stage 2 the noise in the digitized image recorded by the image sensor increases or the signal-noise distance decreases. The quality of the recorded image, however, can nevertheless be sufficient for a predetermined application within the entire stage 2 or up to a threshold value of the gain. In stage 3 the quality of the image recorded by the image sensor is no longer sufficient for many applications and in particular for medical applications.

These results can be obtained without absolutely measuring the individual parts of the optical investigation system, for example light source, light conductor cable, endoscope, video camera and their particular coupling. In particular, therefore, no calibrated measuring devices are required either. In addition, the optical investigation system can be tested in precisely the condition in which it can be used before or after the testing for optical investigation of an object. In particular, also, no light conductor cables or other connections for optical or electrical coupling are required to be severed, modified or converted. In addition, no calibration of the video camera is required because no absolute measurement of the brightness of the image on the image sensor of the camera is necessary, but rather it is possible to draw conclusions immediately from the operating condition of the camera concerning the functionality of the optical investigation system.

In addition to the exposure time and gain, additional parameters can be varied to adapt to an exposure situation that departs from the described example. For example, automatically controlled by the CCU or from outside, the image repetition frequency and thus the maximum exposure time can be varied and/or groups of a varying number of image points can be combined to achieve an improvement of the signal-noise distance with reduced spatial resolution. Both parameters can be varied, for example, simultaneously with the gain within stage 2 or in one or two additional stages between stage 2 and stage 3.

For a more precise and quantitative description of the operating condition of the video camera, an exposure parameter E can be computed from the exposure time T and the gain G, for example on the basis of the formula $E=a \cdot T^b \cdot G^c$. The constants a, b and c result, for example, from geometry, sensitivity and other properties of the video camera system and from a normalization of the exposure parameter E, so that for example in the maximum exposure time and the minimal gain the exposure parameter is $E=1$. The constants b, c each lie, for example, between 0.3 and 3, in particular between 0.5 and 2. In the simplest case, $b=c=1$ and thus $E=a \cdot T \cdot G$.

Depending on the structure and functioning of the video camera, for various areas of the image sensor or for various areas of the image recorded by the video camera or for various color channels, equal or different operating conditions can exist. In testing the optical investigation system, one or more areas or color channels can be selected in this case or the operating conditions of the video camera in various areas or color channels can be linked with one another logically or algebraically.

Instead of recording the operating condition of the video camera by calling up the existing parameters, the operating condition can also be recorded by determining the noise level or the signal-noise distance in the recorded image. The noise level is, for example, essentially constant within the stage 1 described above and increases within stages 2 and 3 with decreasing brightness of the image on the image sensor. Therefore the operating condition of the video camera can also be recorded by the noise level when the aforementioned parameters are not, or are only partly, called up directly or callable directly.

In a method for testing an optical investigation system with a light source, an imaging device and a video camera for optical investigation of an object, a reference surface with predetermined properties is illuminated with illuminating light from a light source. An image of the reference surface is recorded by means of the imaging device and video camera. An operating condition of the video camera, which is in existence during the recording of the image, is recorded. The functionality or another property of the investigation system is determined on the basis of the recorded operating condition.

The optical investigation system is in particular an endoscopy system for medical or technical, non-medical, applications, where the imaging device is an endoscope. Endoscopes for non-medical applications are also designated as boroscopes. The video camera can be present in the form of a separate unit, optically coupled with the imaging device. Alternatively, the video camera can be, for example, integrated into the imaging device.

The reference surface and its optical properties are, in particular, unchangeable or stable over time. The reference surface can approximate a Lambertian radiator, or reflect incident light in a manner that approximates ideal diffusion. The light source can be integrated into the imaging device, for example in the form of a light diode on the distal end of an endoscope. Alternatively, the light source can be executed as a separate device that, for example, is coupled by a light conductor cable with the imaging device or whose light is conducted by other means onto the object that is to be investigated or onto the reference surface.

The described test method makes possible a simple and rapid testing of the functionality of an optical investigation system. Calibrated or gauged measurement apparatuses are not required.

The described test method is applicable in many cases to an optical investigation program in the condition in which it has been or will be put to use before or afterward, for example in medical diagnostics. With the described test method it is therefore possible, for example, to establish simply and rapidly whether all components of the investigation system are coupled with one another functionally and perfectly. For example, an insufficient optic coupling of an external light source, executed as a separate device, with an endoscope has an impact on the illumination of the object to be investigated or of the reference surface because of a defective light conductor cable or a faulty plug-in connection. The insufficient illumination also has an effect on the operating condition of the video camera and can therefore be recognized with the described test method.

With a method as described here the distal end of the imaging device can be positioned at a predetermined position, in particular also in a predetermined direction, relative to the reference surface and can be in such position during the illumination and recording of the image. This arrangement at a predetermined position and possibly in a predetermined direction can be supported by a positioning device, which guides and holds the imaging device, and in particular its distal end. Alternatively, for example on the reference surface, one or more optically recognizable marks can be placed, so that the distal end of the imaging device is positioned relative to the reference surface in such a way that the marks lie at predetermined sites in the recorded image, for example on the edge. These marks can simultaneously take over other functions, for example the focusing of the imaging device on the reference surface or—in particular because of its spectral properties—can simplify the identification of illumination and observation filters of the optical investigation system.

The arrangement of the distal end of the imaging device at a predetermined position and possibly in a predetermined direction improves the precision with which the optical investigation system can be tested. For this purpose the predetermined position and possibly the predetermined direction correspond, for example, to the typical distance or to a maximum distance between the distal end of the imaging device and the observed object in an application foreseen for the optical investigation system.

In every one of the methods described here, in addition, it is possible to record an application foreseen for the optical investigation system and to ascertain a requirement associated with the foreseen application of the optical investigation system. A requirement is associated with every application in such a way that the functionality of the optical investigation system for the application or another predetermined property of the optical investigation system prevails if the operating condition that prevails during the recording of the image of the reference surface corresponds to the associated requirement. For example, medical-diagnostic investigations in body cavities of various size or of organs with various optical properties can place various demands on the optical investigation system. These various demands can become apparent because of various requirements for the operating condition of the video camera that prevails during the recording of the image of the reference surface.

In every one of the methods described here, the reference surface can be illuminated with irradiance or with an illuminating strength that is equal to a predetermined fraction of the irradiance applied in the foreseen application of the optical investigation system. This is achieved, for example, by dimming the light source or by using a diaphragm, grid or filter. Because of this reduced irradiance, it is possible to take into account the fact that the object observed in the foreseen use of the optical investigation system has a lesser remission factor than the reference surface. Therefore, to execute the test method, not only can the reference surface be adapted to the foreseen use of the optical investigation system that is to be tested, but alternatively the irradiance of the reference surface can be adapted to the foreseen use, so that the second way can be simpler, depending on the light source and its control device. The methods described here allow in this way a highly differentiated testing of an optical investigation system.

In every one of the methods described here, the recording of the operating condition can include ascertainment of an exposure parameter, and the determination of the functionality or of another property can include comparison of the ascertained exposure parameter with a predetermined threshold value. The exposure parameter E, for example, is calculated according to the formula $E=a \cdot T^b \cdot G^c$ already described on the basis of exposure time T and gain G. In comparison to the differentiation of the operating condition by stages as also described above, calculation of an exposure parameter permits a more precise quantification and finer differentiation. The threshold value, for example, depends on the foreseen use of the optical investigation system. By the choice of the threshold value, for example, it is possible to take into account the optical properties of an object to be observed in the foreseen use of the optical investigation system, in particular the remission factor, the fluorescence-quantity yield and its wavelength dependency, as well as contrasts, and its differences with respect to the reference object.

In every one of the methods described here, the reference surface can be illuminated successively with illuminating light with a first illumination spectrum and with illuminating light with a second illumination spectrum. A first operating condition of the video camera, which prevails during the recording of an image with illumination of the reference surface with the illuminating light with the first illumination spectrum, and a second operating condition of the video camera that prevails during the recording of an image with illumination of the reference surface with the illuminating light with the second illumination spectrum are recorded. The functionality or another property of the optical investigation system is determined on the basis of the first operating condition and the second operating condition. This can be especially useful when the optical investigation system is to be used to record fluorescence (for example in PDD or in AF diagnostics).

For example, the light source, by filters that can be inserted manually or mechanically into the illumination beam path, is configured to provide alternatively a spectrum, which is at least approximately white, of visible light and one or more spectra to excite fluorescence of various fluorophores. If the use foreseen for the optical investigation system calls for the recording of fluorescent light, the imaging device must comprise an observation filter or a corresponding filter characteristic, which is adapted to the spectrum of the illuminating light or to the illumination filter. By illuminating the reference surface with illuminating light with various spectra and recording the operating condition of the video camera that prevails in each case, it is possible to ascertain which observation filter or which filter characteristic is comprised by the observation beam path of the imaging device. This makes possible a simple, rapid and reliable verification as to whether the optical investigation system includes the correct observation filter or the correct imaging device with the correct filter characteristic of the observation beam path.

In every one of the methods described here, in addition, it is possible to record a first operating condition of the video camera during the recording of an image of the reference surface while using a first observation filter or an imaging device with a first filter characteristic of the observation beam path and to record a second operating condition of the video camera during the recording of a second image while using a second observation filter or an imaging device with a second filter characteristic of the observation beam path. On the basis of the two operating conditions, the illumination spectrum or the employed illumination filter can be determined. Thus, for example, the error-free functioning of a mechanical control unit of the illumination filter can be verified or a manually applied illumination filter can be identified.

By recording several operating conditions of the video camera while recording images using various illumination filters and/or observation filters, additional detailed information can be obtained on properties of the optical investigation system. To the extent that the illumination filter or observation filter can be controlled and reproducibly exchanged, it is possible to draw unequivocal conclusions concerning the respective other filter and/or the functionality of a device for exchanging the filter.

In every one of the methods described here, in which several operating conditions are recorded with various illumination filters and/or with various observation filters, the determination of the functionality or of another property of the optical investigation system can include ascertainment, in particular a computation, of an indicator parameter from the recorded operating conditions and a comparison of the ascertained indicator parameter with one or especially several threshold values. For example, an exposure parameter is ascertained from each of the recorded operating conditions, as described above. The exposure parameters are then logically or algebraically linked, for example by forming a ratio or a difference, which forms the indicator parameter.

In every one of the methods described here, the recording of an operating condition can include recording of one operating condition for each of a number of color channels. In addition, recording of an operating condition can include ascertaining of an exposure parameter for each of the number of color channels. This is particularly true when the video camera being used foresees or makes possible the independent selection of various exposure times and/or gains for various color channels. The recorded operating conditions or exposure parameters, which are associated with various color channels, can in turn be logically or algebraically linked and then compared, for example with a threshold value, to determine functionality or another property of the optical investigation system. In particular, the recorded operating conditions or exposure parameters are logically or algebraically linked and then compared with several threshold values.

In every one of the methods described here, the recording of an operating condition can include recording of a white balance parameter. White balance parameters can be obtained or selected during an ongoing manual or—automatically or manually triggered or controlled—automatic white balance. White balance parameters describe or determine, for example, the proportions of exposure times, gains or exposure parameters of the individual color channels or constitute correction factors that are to be applied during or after digitization of the image. On the basis of the white balance parameters, for example, it can be easily and reliably determined whether the illuminating light from the light source is (approximately) white or includes predominantly short wavelengths for exciting fluorescence.

Depending on the optical properties of the reference surface, more detailed information on the properties of the investigation system, in particular illumination filters and observations filters, can be obtained on the basis of the operating conditions or exposure parameters associated with the individual color channels or on the basis of one or more white balance parameters.

The reference surface in each of the methods described here can be white or gray, or can have a remission factor that is essentially wavelength independent, especially within the spectral range visible to the human eye. Alternatively, the reference surface can be colored or can have a wavelength dependent remission factor. Alternatively or in addition, the reference surface can be fluorescent. The reference surface can have unified or homogeneous optical properties or can include areas with different optical properties. As is described hereinafter with reference to the drawings, a reference surface having several areas with different optical properties can make possible an even more detailed or more precise determination of properties of the optical investigation system.

In every one of the methods described here, the recording of an operating condition can include recording of a noise level or of a signal-noise distance in the recorded image. From the noise level, as already described, conclusions can be drawn about the operating condition of the video camera. Thus the operating condition of the video camera can also be recorded if the parameter or parameters that determine it cannot be directly acquired or are not otherwise accessible.

In every one of the methods described here, in addition, patient data can be recorded and information on the functionality or on another property of the optical investigation system and the patient data can be filed in a database. By integrating the test method with the recording and storage of patient data, it is possible to ensure that with every medical-diagnostic application of the optical investigation system, said system is tested with respect to its functionality and/or to another property and the result of the testing is documented individually or in relation to the patient. The test method can thus become a reliable, non-manipulatable component of quality assurance in everyday clinical practice.

In every one of the methods described here, after determination of the functionality or of another property of the optical investigation system, a report can be displayed. This report reveals the functionality or the degree of functionality and/or of another determined property of the investigation system. Alternatively or in addition, the report can contain an operating instruction or an operating recommendation. For example, the report can include a demand to check plug-in connections between a light conductor cable and the light source or imaging device or to exchange the imaging device or an observation filter and then to repeat the testing of the optical investigation system. After repeated establishment of faulty functionality, other instructions or recommendations can be reported, for example a recommendation of immediate or prompt replacement of the light source.

The present invention can be implemented as a method or as a computer program with program code for executing or control of such a method if the computer program runs on a computer or processor. In addition, the invention can be implemented as a computer program product with a program code stored on a mechanically readable carrier (for example, an ROM, PROM, EPROM, EEPROM or Flash storage device, a CD-ROM, DVD, HD-DVD, Blue Ray DVD, diskette or hard drive) or in the form of firmware for executing one of the aforementioned methods if the computer program product runs on a computer, calculator or processor. In addition the present invention can be implemented as a digital storage medium (for example, ROM, PROM, EPROM, EEPROM or Flash storage device, CD-ROM, DVD, HD-DVD, Blue Ray DVD, diskette or hard drive) with electronically readable control signals that can interact with a programmable computer or processor system in such a way that one of the described methods is executed.

In addition the present invention can be implemented as a control device for an optical investigation system with an imaging device, in particular an endoscope, a video camera and a light source for optical investigation of an object, where the control device is configured to execute one of the described methods, or where the control device includes a computer program, a computer program product or a digital storage medium, as described in the preceding paragraph. The control device can be a video camera control or can be integrated therein.

BRIEF DESCRIPTION OF THE DRAWINGS

Embodiments are explained in more detail hereinafter with reference to the drawings.

FIG. 7 shows a schematic depiction of additional white balance parameters.

FIG. 8 shows a schematic depiction of a flow diagram.

DETAILED DESCRIPTION OF THE INVENTION

Figure 1:
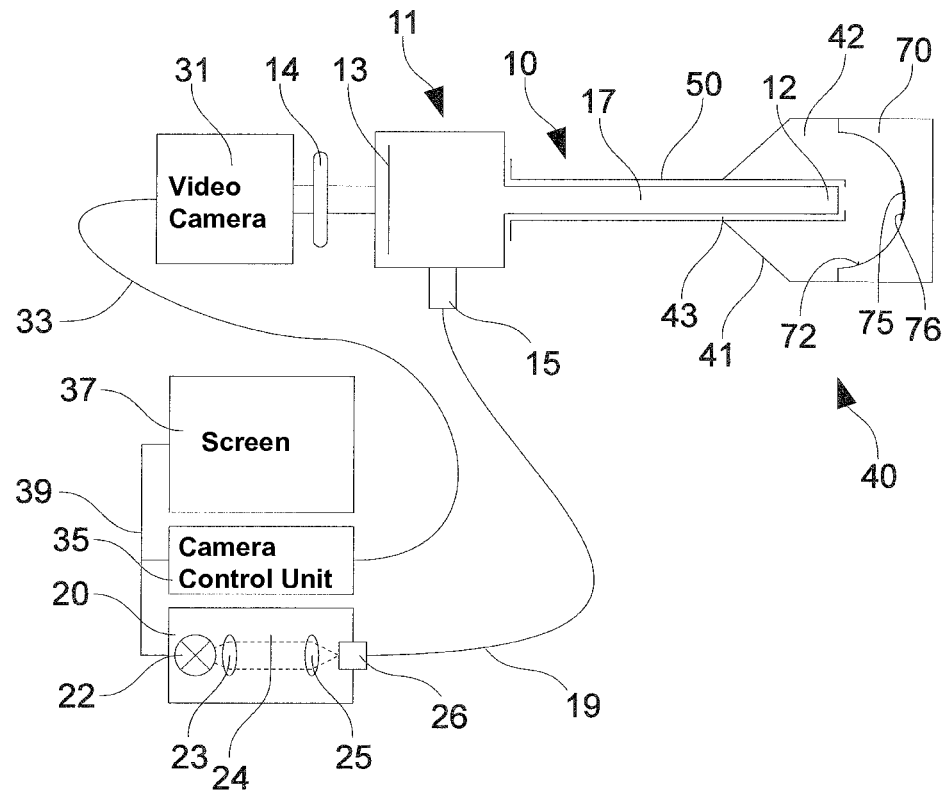
FIG. 1 shows a schematic depiction of an optical investigation system.

FIG. 1 shows a schematic depiction of an optical investigation system. The optical investigation system in this example is an endoscopy system, which can be applied, for example, in medical-diagnostic methods in urology and in other specialties. The endoscopy system includes an endoscope 10 with a proximal end 11 and a distal end 12. The endoscope 10 includes an illumination or excitation beam path and an observation beam path, which are not shown in detail in FIG. 1. The illumination beam path includes in particular one or more lightwave conductors to transmit illumination or excitation light from the proximal end 11 to the distal end 12 and a light outlet on the distal end 12 through which illumination light can exit from the distal end 12 of the endoscope 10 in order to illuminate an object to be observed. The observation beam path includes a light inlet on the distal end 12 of the endoscope 10, a lens to transmit observation light emitted from an observed object, from the distal end 12 to the proximal end 11, an observation filter 13 and an eyepiece 14. To transmit the observation light from the distal end 12 to the proximal end 11 of the endoscope 10, a rod lens system, for example, or an oriented bundle of lightwave conductors is provided in a shaft 17 of the endoscope 10. The endoscope 10 in addition comprises on its proximal end 11 a coupling 15 for mechanical and optical coupling of a light conductor cable 19 with the described illumination beam path in the endoscope 10.

The endoscope 10 is coupled with a light source apparatus 20 by the light conductor cable 19. The light source apparatus 20 includes a light source 22, for example a halogen lamp, a high-pressure gas discharge lamp, a light diode or a laser. In addition the light source apparatus 20 includes a first converging lens 23, an illumination filter 24 and a second converging lens 25. The light source 22 is coupled with the light conductor cable 19 by the first converging lens 23, the illumination filter 24, the second converging lens 25 and a coupling 26.

A video camera 31 is coupled mechanically or optically by the eyepiece 14 with the endoscope 10 and its observation beam path. The video camera 31 includes a light-sensitive image sensor, for example a CCD or CMOS sensor, to convert light falling onto the image sensor into analog or digital electrical signals. By means of a signal cable 33, the video camera 31 is coupled with a camera control unit 35, designated as CCU, to transmit analog or digital electrical or optical signals.

The light source apparatus 20, camera control unit 35, and a screen 37 are coupled with one another by a communication bus 39 or several separate signal lines. By means of the communication bus 39, additional apparatuses, not shown in FIG. 1, can be coupled with the light source apparatus 20, the camera control unit 35 and the screen 37 inside or outside the treatment area in which the endoscope system is installed; examples include a database, a keyboard, a computer mouse and other user interfaces.

Also shown in FIG. 1 is a test apparatus 40 with a light-insulated housing 41, a hollow space 42 in the light-insulated housing 41 and an aperture 43 to the hollow space 42. The distal end 12 of the endoscope 10 is introduced through the aperture 43 into the hollow space 42 of the test apparatus 40. A positioning device 50 located in the aperture 43 holds the shaft 17 of the endoscope 10 by form-locking or force-fitting, in such a way that the distal end 12 of the endoscope 19 is positioned in a predetermined position and in a predetermined direction in the hollow space 42. In addition, the positioning device 50, at least when the shaft 17 of the endoscope 10 is mounted in the positioning device 50, to a great extent prevents the penetration of light from the environment through the aperture 43 into the hollow space 42 in the housing 41.

In addition, a reference body 70 with a reference surface 72 is positioned in the hollow space 42 of the test apparatus 40. The reference surface 72 has predetermined optical properties and the spatial shape of a portion of a spherical surface or of a cylindrical mantle. The position foreseen for the distal end 12 of the endoscope 10 is situated in particular at the center point of this spherical surface or on the axis of symmetry of the cylindrical mantle. In particular, the main point on the object side, or the point of intersection of the optical axis with the object-side principal plane of the imaging device 10, stands at the center point of the spherical surface or on the axis of symmetry of the cylindrical mantle.

The reference surface 72 has predetermined optical properties that are unchangeable or stable over time. The reference surface 72 can be white or can have a remission factor that is essentially wavelength independent in the spectral range visible to the human eye. The reference surface 72 can alternatively be in color or can have a wavelength dependent remission factor in the spectral range visible to the human eye. Alternatively or in addition, the reference surface 72 can be fluorescent. Here the wavelengths that are required for excitation of fluorescence, are situated for example, in the ultraviolet or, preferable for medical applications, in the blue spectral range and the emitted fluorescent light is in the green, red or infrared spectral range. The optical properties can be homogeneous or location-independent over the entire reference surface 72.

Alternatively the reference surface comprises several areas with various optical properties. In the example shown in FIG. 1, the reference surface 72 is predominantly white with an indicator area 75 and a reference area 76, which each have optical properties that differ from those of the rest of the reference surface 72. The indicator area 75 and reference area 76, with sharp edges or on the basis of their arrangement or shape, can simplify or make possible a focusing or a selection of the focal distance or size of the field of vision of the imaging device. In addition the optical properties of the indicator area 75 and of the reference area 76 can simplify a determination of the transmission spectrum of the illumination filter 24 and of the transmission spectrum of the observation filter 13. The reference body 70, apart from the indicator area and the reference area 76 on the reference surface 72, consists in particular of polytetrafluorethylene PTFE, which in particular is marketed by DuPont under the brand name Teflon, or of silicon. Both PTFE and silicon can be filled with white or colored pigments or dyes.

Figure 2:
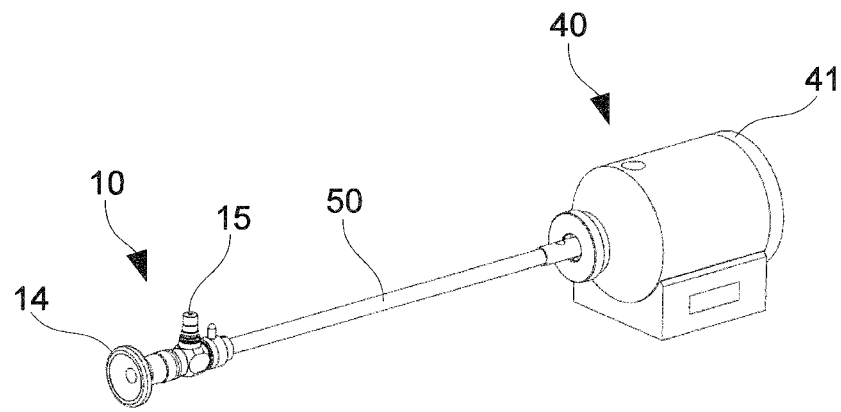
FIG. 2 shows a schematic depiction of an endoscope with a test apparatus.

FIG. 2 shows a schematic axonometric view of an endoscope 10 and of a test apparatus 40 that are similar to the endoscope and test apparatus that were presented above with reference to FIG. 1. Contrary to FIG. 1, no separate light source, video camera or other apparatuses are shown. The exact positioning of the distal end of the endoscope 10 in the test apparatus 40 is achieved in this example by form-locking between the positioning device 50 and the distal end 11 of the endoscope 10, in particular by means of a mechanical stop or a catch-locking connection.

The test methods described hereinafter are also applicable to optical investigation systems and test apparatuses that differ from those illustrated in FIGS. 1 and 2. For example, the test methods are applicable regardless of whether a light source and/or a video camera are separate units that can be coupled with the endoscope or are integrated in the endoscope at its proximal or distal end. In addition, the test methods are applicable when the excitation or illuminating light is conducted not by the endoscope or generally by the imaging device, but rather in other manner onto the object to be observed or onto the reference surface. The arrangement of illumination and observation filters can also differ from the examples presented above with reference to FIGS. 1 and 2. For the sake of greater clarity, reference numbers from FIGS. 1 and 2 are nevertheless used hereinafter by way of example.

In a first test method for an optical investigation system, the distal end 12 of an imaging device 10 is inserted into a hollow space 42 in a housing 41 of a test apparatus 40. A positioning device 50 holds the imaging device 10, in particular its distal end 12, by force-locking and/or form-locking at a predetermined position and in a predetermined direction relative to a reference surface 72. The reference surface is in particular white or has a remission factor that is essentially wavelength independent within the spectral range visible to the human eye.

The reference surface 72 is then illuminated with illuminating light from a light source 22. In addition to the spectral properties of the light source 22, an illumination filter 24 in the illumination beam path determines the spectrum of the illuminating light. The illumination filter 24 can be inserted manually or mechanically into the illumination beam path and removed from it. As a rule, several illumination filters 24 are available that can be inserted in alternation into the illumination beam path. The light source 22 generates, for example, a spectrum that is perceived as white by the human eye. If no illumination filter 24 is positioned in the illumination beam path, the reference surface 72 is thus illuminated with white light.

First an illumination filter 24 is inserted that is appropriate for the foreseen application of the optical investigation system. If the optical investigation system is foreseen for observing an object in white light and the light source 22 generates white light, no illumination filter is inserted into the illumination beam path.

In illuminating the reference surface 72 with illuminating light of the foreseen spectrum, a white balance of the video camera 31 can be executed. This white balance can occur manually or automatically, so that an automatic white balance can be controlled or triggered manually or automatically. In the white balance, two white balance parameters, for example, are determined, which are also known as white balance gains (WBG). The first WBG parameter determines the proportion of the gains in the red and green color channels; the second WBG parameter determines the proportion of the gains in the blue and green color channels. The gains are analogous gains before digitization by electric signals arising primarily in the image sensor. Alternatively the WBG parameters determine, for example, the proportion of corrector factors, which are to be applied to digitized signals of the individual color channels.

The described white balance is optional. In many cases, however, it is required or meaningful in order to achieve a natural color impression in a successive application of the optical investigation system. The white balance parameters constitute a part of the operating condition of the video camera 331. If the described white balance is executed, conclusions can be drawn from the values of the white balance parameters concerning properties of the optical investigation system. This is described hereinafter in greater detail with reference to FIGS. 6 and 7.

If the reference surface 72 is not homogeneously white or does not have a remission factor that is wavelength independent for the human eye at all sites, one or more white areas of the reference surface 72 can be selected manually or automatically for the white balance. If a white balance is performed on a non-white reference surface 72 or on a non-white area of the reference surface 72, conclusions can likewise be drawn from the resulting white balance parameters concerning properties of the optical investigation system.

In illuminating the reference surface 72 with the foreseen illuminating light, an image of the reference surface 72 is generated by means of the imaging device 10. This image in illuminating light remitted by the reference surface 72 and in some cases in fluorescent light emitted by the reference surface 72 is spectrally filtered by an observation filter 13. The image generated by the imaging device 10 and in some cases filtered by the observation filter 13 is visually recorded or observed by an eyepiece 14 or recorded by a video camera 31. In recording the image, the video camera 31 itself or the camera control unit 35 selects an operating condition of the video camera 31 in such a way that the recorded image or the analog or digital electric signals correspond to predetermined requirements. These requirements include, for example, a predetermined median value of the brightness values in the entire recorded image or in a partial area of the recorded image. The exposure time and the (especially analog) gain of the primary electric signals before their digitization are the parameters that make up or describe the operating condition of the video camera 31, and typically are selected depending on the brightness of the optical image generated by the imaging device 10 on the image sensor of the video camera 31. Both the exposure time and the gain can have the same values for all image points and all color channels or can have different values for different color channels or different areas of the image sensor.

In illuminating the reference surface 72, one or more parameters of the automatically selected operating condition of the video camera are recorded, for example by scanning or reading out from a storage device. On the basis of the recorded operating parameters of the video camera 31, conclusions can be drawn concerning the exposure situation, in particular the brightness, of the optical image generated by the imaging device 10 on the image sensor of the video camera 31. Minimum values exist for this brightness that can be dependent on the expected application of the optical investigation system. The optical image generated by the imaging device 10 on the image sensor of the video camera 31 fulfills the requirements and is in particular sufficiently bright, when there is completely correct configuration of the optical investigation system and in particular if all components are connected or coupled with one another with complete functionality and without error and if both the illumination and the observation filters correspond to the expected application.

If the operating condition of the video camera 31 fulfills a predetermined requirement (for example, to lie in stage 1 as described above) it can be concluded that there is an unrestricted functionality of the optical investigation system. If the recorded operating condition of the video camera 31 does not correspond to the predetermined requirement (for example, lies in either of steps 1 or 2 as described above), it can be concluded that the optical investigation system is not functional, or is not functional without restriction. For example, the light source 22 delivers too low a beam of light, the light conductor cable 19 is defective or not coupled perfectly with the light source 22 or the imaging device 10, the imaging device 10 is defective, a wrong illumination filter is positioned in the illumination beam path, or a wrong observation filter is positioned in the observation beam path.

The application for which the optical investigation system is intended can be recorded at any desired time before comparing the recorded operating condition of the video camera 31 with the predetermined requirement. For this purpose, in particular, an entry at a user interface is recorded after a corresponding demand. Because different applications of the optical investigation system make different demands on the quality of the recorded images, various requirements concerning the required operating condition can be associated with various applications. The requirement that must be met by the recorded operating condition of the optical investigation system is ascertained as the requirement associated with the recorded expected application. The requirement includes, for example, one or more threshold values for the operating condition, in particular threshold values for the exposure time, for the gain or for an exposure parameter calculated from it.

After the described determination of the functionality of the investigation system for the expected application, a corresponding report can be issued via a user interface. This report can include operating instructions or operating recommendations. For example, if the operating condition does not meet the requirement, a demand is issued to test the components of the optical investigation system and their coupling or to exchange the light source 22 or another component and to repeat the test process.

The precision of the described test method can be increased, for example, by computing an exposure parameter from the operating condition of the video camera, in particular from the exposure time, the gain and/or additional parameters. The exposure parameter E is computed, for example, according to the already mentioned formula $E=a \cdot T^b \cdot G^c$. On the basis of the exposure parameter, a detailed account of the functionality of the optical investigation system and a more precise operating recommendation can be expressed. For example, it becomes possible to distinguish whether the optical investigation system is suitable without restriction, with restriction, or not suitable at all. The exposure parameter can be filed or stored. On repeated testing of the same optical investigation system, a trend or a development of the exposure parameter over time can be ascertained, which for example can be traced back to an ageing process of the light source 22. From the stage of the ageing process of the light source 22, a recommendation is given, for example, to exchange it or to adopt restrictions in operating the light source 22.

In the framework of the described test method, in particular by a user interface, patient data can be recorded and then filed in a database along with the result of the test method and in particular with the result of an ensuing examination of the patient by means of the optic investigation system. This ensures that the optic investigation system before or after the examination of a patient is tested for its functionality and that the result of this test is logged or documented.

The requirements or threshold values, which are associated with the various applications of the optical investigation system, for the operating condition or for the parameters that characterize the operating condition, can be determined empirically in that medical personnel conduct investigations that correspond to the expected application under real conditions or with various illumination situations and evaluate the quality of the image of the observed object.

An object that is to be observed in an expected application of the optical investigation system can have a remission factor and other optical properties that differ from those of the reference surface 72. During the test process described above, this can be taken into account by changing or adjusting the brightness of the light source 22 during the test process, for example by dimming or by the use of a diaphragm, grid or filter. In particular, the available light flow is reduced by a factor that corresponds to the ratio between the remission factor of an object relevant in the expected application of the investigation system and the remission factor of the reference surface 72.

If the video camera 31 being used so allows, in the test method described above either the exposure time or the gain can be firmly set in advance and only the respective other parameter that is being selected can be recorded and evaluated corresponding to the description given above.

Hereinafter, other variants of the test method described above are presented, which are applicable, for example, when the expected application of the optical investigation system is PDD, AF diagnostics or another fluorescence diagnostics. For clarification, fluorescence excitation and de-excitation and transmission spectra of illumination and observation filters for the fluorescence diagnostics are described first. For example, the filters used for PDD and for AGF diagnostics differ from one another, but are easily interchangeable in visual observation. The test method described above can be modified in such a way that the filters in use can be identified.

Figure 3:
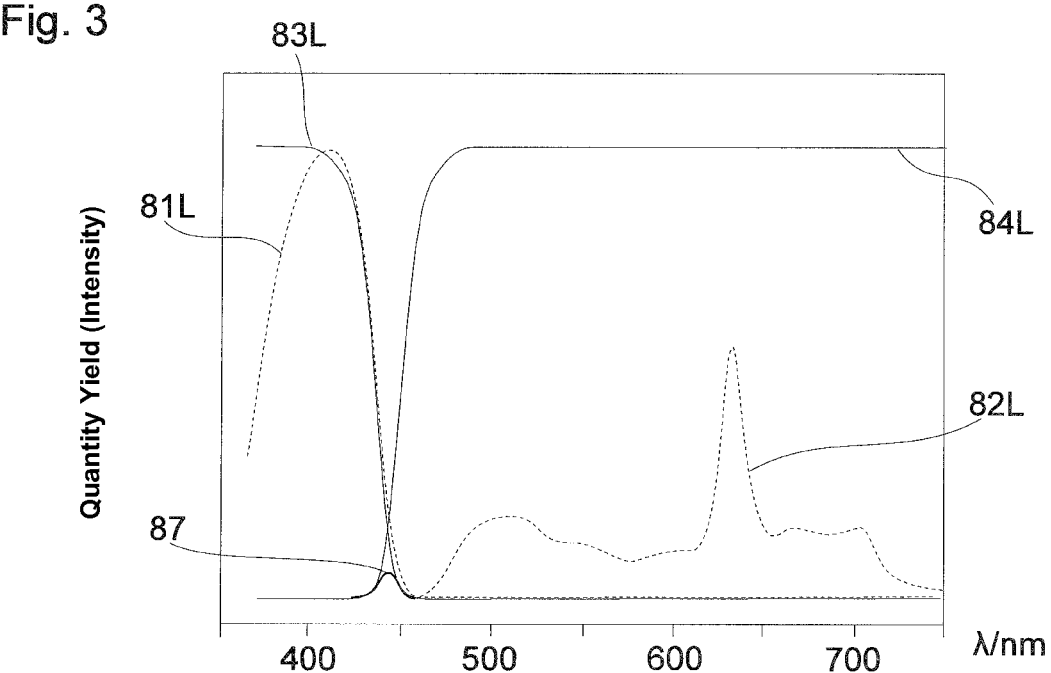
FIG. 3 shows a schematic depiction of several spectra.

FIG. 3 shows a schematic depiction of a fluorescence excitation spectrum 81L and of a fluorescence de-excitation spectrum 82L from fluorescence of protoporphyrin IX induced by 5-aminolevulinic acid (ALA). The wavelength lambda is assigned to the abscissa axis and quantity yield or intensity to the ordinate axis in arbitrary units. Also depicted are a transmission spectrum 83L of an appropriate illumination filter 24 and a transmission spectrum 84L of an appropriate observation filter 13. For the transmission spectra 83L and 84L, the transmittance degree in each case is assigned to the ordinate axis.

In addition, the product 87 of transmission spectra 83L, 84L or the transmission spectrum of the successively switched-on illumination and observation filters is depicted. The filter edges of the illumination filter 24 and of the observation filter 23 are selected so that the product of their transmission spectra in a small wavelength range is not zero, and is also designated as the overlap area. A small portion of the illuminating light that strikes the observed object can therefore be observed by the observation filter 13. The observed object therefore is also recognizable without fluorescence in (without wavelength displacement) remitted blue illumination light. Fluorescence, on the other hand, appears primarily in the green and red spectral range. Thus there is a clear color contrast between fluorescent and non-fluorescent areas of an object observed by means of the optic investigation system.

Figure 4:
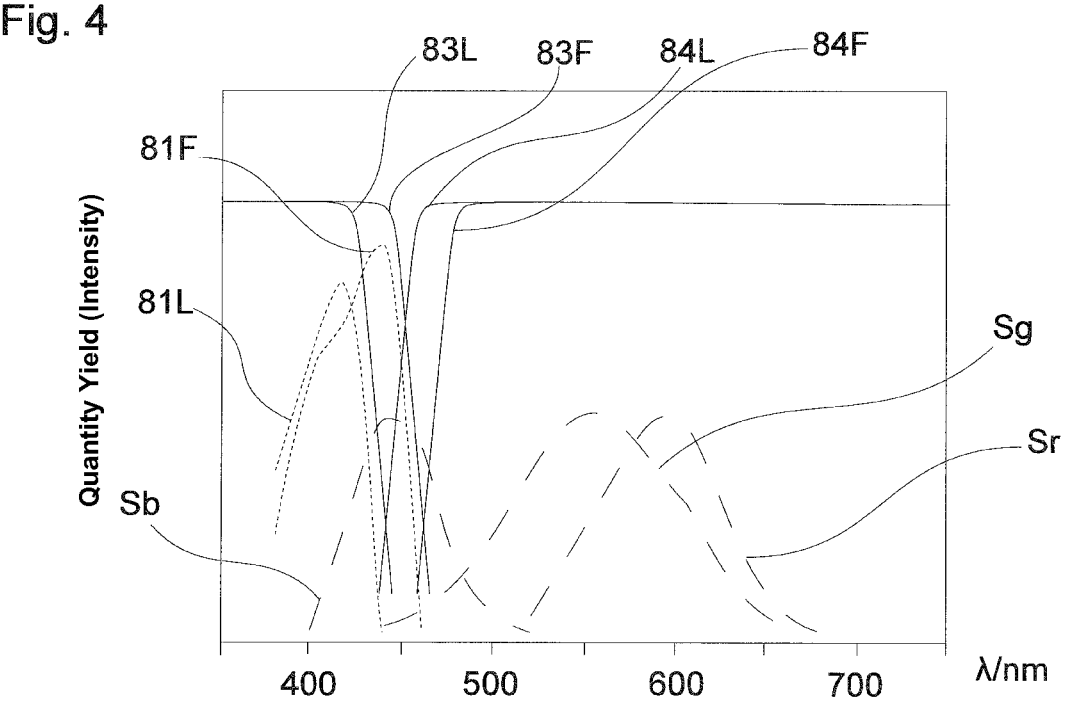
FIG. 4 shows a schematic depiction of additional spectra.

FIG. 4 is a schematic depiction of fluorescence-excitation spectra as well as transmission spectra of illumination and observation filters, which are used for various types of fluorescence diagnostics. The wavelength lambda is plotted on the abscissa axis. In addition to the fluorescence-excitation spectrum 81L, the transmission spectrum 83L, the illumination filter and transmission spectrum 84L of the observation filter for PDD, the figure also shows the fluorescence-excitation spectrum 81F, the transmission spectrum 83F of the illumination filter and the transmission spectrum 84F of the observation filter for observing autofluorescence (AF) of tissue.

In addition, FIG. 4 shows spectral sensitivities Sb, Sg, Sr of the blue, green and red color receptors of the human eye. Because cameras as far as possible are adapted to the color reception of the human eye, as a rule they have similar spectral sensitivities or separate the color channels even more sharply. In comparing the transmission spectra 83L, 83F, 84L, 84F of the illumination and observation filters for PDD and AF with the spectral sensitivities of the color receptors of the human eye, it becomes clear that the small differences between the transmission spectra of the illumination and observation filters for PDD and AF are recognizable to the human eye only under good conditions in immediate comparison—which is seldom possible.

Figure 5:
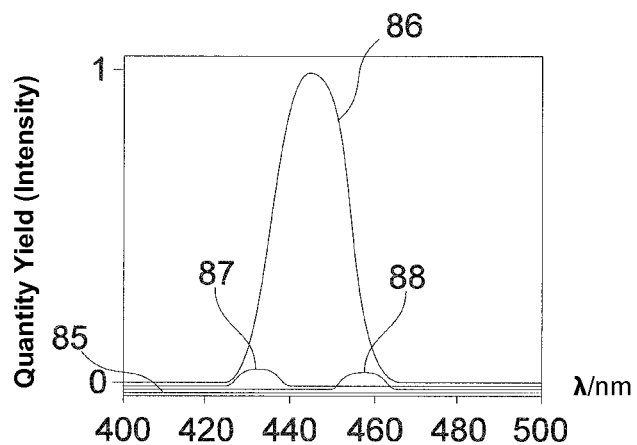
FIG. 5 shows a schematic depiction of products of transmission spectra.

FIG. 5 shows a schematic depiction of various products, each of a transmission spectrum of an illumination filter and of a transmission spectrum of an observation filter. The curves are vertically slightly pushed toward one another so that they can be distinguished more easily. In fact, all products at wavelengths around 400 nm and at wavelengths around 500 nm are close to zero.

The product 85 of the transmission spectrum 83L of the PDD illumination filter and the transmission spectrum 84F of the AF observation filter is very small or nearly zero for all wavelengths. Thus the AF observation filter is not transparent for remitted PDD excitation light.

The product 86 of the transmission spectrum 83F of the illumination filter for AF diagnostics and the transmission spectrum 84L of the observation filter for PDD is clearly greater than zero for wavelengths in the range from about 430 nm to about 460 nm. The PDD observation filter is thus transparent for remitted AF excitation light to a clearly visible degree.

The product 87 of the transmission spectrum 83L of the illumination filter for PDD and the transmission spectrum 84L of the observation filter for PDD is, as already shown above with reference to FIG. 4, not zero in a small wavelength range between about a 430 nm and about 440 nm. The PDD observation filter is slightly transparent for remitted PDD excitation light.

The product 88 of the transmission spectrum 83F of the illumination filter for AF and the transmission spectrum 84F of the observation filter for AF is not zero in a small wavelength range in the area of 460 nm. The AF observation filter is slightly transparent for remitted AF excitation light.

Regarding a white, non-fluorescent reference surface with an optic investigation system, it can thus be clearly distinguished under favorable circumstances whether a PDD illumination filter is combined with an AF observation filter or an AF illumination filter is combined with a PDD observation filter. In the first case, an extremely dark image is observed; in the second case, too bright an image is observed in comparison to correct combinations of illumination filter and observation filter. It can scarcely be distinguished whether an illumination filter for PDD is combined with an observation filter for PDD or an illumination filter for AF with an observation filter for AF. In both cases the image is approximately equally bright; the difference in wavelength in any case can be distinguished by the human eye in very good conditions in an immediate comparison.

The test method described above can be modified in such a way that the illumination filter and the observation filter can be identified as an additional property of the optical investigation system. The following table shows the exposure parameter E for all possible combinations of a white light or standard illumination (STD; first row), of a PDD illumination filter (second row) or of an AF illumination filter (third row) with a standard endoscope for observing in remitted white light (first column), a PDD endoscope (second column) or an AF endoscope (third column). The standard endoscope, both in the illumination and in the observation beam path, has a transmission that is as completely wavelength independent as possible in the wavelength range visible to the human eye or that appears essentially not to be tinged to the human eye. The PDD endoscope, in the observation beam path, has an observation filter with the transmission spectrum 84L described above with reference to FIG. 4, or the observation beam path has, without a dedicated observation filter, a corresponding filter characteristic. The AF endoscope in the observation beam path has an observation filter with transmission spectrum 84F as described above with reference to FIG. 4, or the observation beam path of the AF endoscope has, without a dedicated observation filter, a corresponding filter characteristic.

| E | STD endoscope | PDD endoscope | AF endoscope |
| --- | --- | --- | --- |
| STD illumination | 0.0023 | 0.0030 | 0.0033 |
| PDD illumination | 0.0020 | 2.50 | "∞" |
| AF illumination | 0.0014 | 0.0344 | 2.50 |

A difference that is clearly recognizable in many situations exists between a combination of PDD illumination and AF endoscope (exposure parameter E is very large or endless) on the one hand and the admissible combinations of PDD illumination and PDD endoscope or of AF illumination and AF endoscope (in both cases the exposure parameter is approximately 2.5) on the other hand. A difference, clearly recognizable as a rule, exists between the admissible combinations of PDD illumination and PDD endoscope or of AF illumination and AF endoscope on the one hand and the other combinations, in which the exposure parameter assumes values that are clearly less than 1. The cited figures, however, are only examples, which have been measured in an individual optical investigation system. After each modification of the optical investigation system or on other optical investigation systems, differing values of the exposure parameter E than these can be obtained.

For an optical investigation system with a certain endoscope (either standard endoscope or PDD endoscope or AF endoscope), three different exposure parameters E are now ascertained for three different spectra of the excitation or illuminating light (white or standard STD; PDD; AF) and ratios are obtained for the exposure parameters E. These ratios are given in the following table.

| | STD endoscope | PDD endoscope | AF endoscope |
| --- | --- | --- | --- |
| $E_{PDD}/E_{STD}$ | 0.84 | 832 | "∞" |
| $E_{AF}/E_{STD}$ | 0.61 | 11.5 | 755 |
| $E_{PDD}/E_{AF}$ | 1.38 | 72.6 | "∞" |

It can be recognized that the three different endoscopes are distinguishable in each of the three ratios of the exposure parameter E. In addition, by forming ratios the influence of other components of the optical investigation system is suppressed, in particular the influence of the light conductor cable 19, its coupling to the light source 22 and to the endoscope 10, the distance from the reference surface 72, and so on. Thus there is no further necessity for a precise positioning of the distal end 12 of the endoscope or of the imaging device in relation to the reference surface 72.

The test method described above can be modified as follows to identify the endoscope used in the optical investigation system that is to be tested (or its corresponding imaging device). Images of the reference surface 72 are recorded successively with two different illumination spectra, for example at white light illumination or without illumination filter and with a PDD illumination filter with the transmission spectrum 83L presented above with reference to FIG. 4 in the illumination beam path. The prevailing operating conditions of the video camera 31 are recorded for both recorded images and from them one exposure parameter $E_{STD}$ or $E_{PDD}$ is calculated by the aforementioned formula $E=a \cdot T \cdot G$. Finally one tests whether the ratio $E_{STD}/E_{PDD}$ is closer to the value (approx. 1) necessary for a standard endoscope or closer to the value (approx. 800) valid for a PDD endoscope or is essentially still greater. If the value of the ratio $E_{STD}/E_{PDD}$ is essentially greater than 800, the optical investigation system in all probability includes an AF endoscope; if the ratio $E_{STD}/E_{PDD}$ is the proximity of 800, then a PDD endoscope is present, and if the ratio $E_{STD}/E_{PDD}$ is 1, a standard endoscope is present.

The described method is especially advantageous and, above all, can be executed especially rapidly if the light source apparatus 20 of the optical investigation system provides for a mechanical replacement of the illumination filter 24. The method can, however, be executed, for example, with a manual replacement of the illumination filter 24 or a corresponding exchange of complete light source apparatuses 20, each with firmly installed illumination filters or unchanging illumination spectra.

Accordingly, in an optical investigation system the illumination filter or the illumination spectrum can be identified. First, images of the reference surface are recorded with two different endoscopes or with two different observation filters. In the process, the prevailing operating condition of the video camera is recorded each time. Two exposure parameters are calculated from the operating conditions. On the basis of the ratios from the two exposure parameters, the illumination filter can be identified.

Although with true endoscopy systems and other optic investigation systems the values of the exposure parameters and their ratios scatter, the described model calculations show that the method is suitable for identifying the observation filter or the illumination filter. In particular, the scattering of the measured ratio $E_x/E_y$ is clearly smaller than the distances of the typical values of the ratios $E_x/E_y$. Consequently the method is very robust.

Hereafter another variant of the test method is described with which the observation filter and/or the illumination filter can be identified. This method can be performed in particular when the operating condition of the video camera 31 can be recorded differentiated by color channels, that is, for example, for every color channel the exposure time and/or the gain can be recorded separately. The method can also be executed, however, when the operating condition or the exposure time and gain are not selected separately and cannot be recorded for every color channel, but rather, for example, are selected in common and equally for all color channels.

In this variant of the test method, the video camera or the camera control unit independently selects exposure time, gain or other parameters, or these parameters are prescribed from outside. Then, for every color channel an accumulator value is selected for the recorded image from the video camera or the camera control unit. The accumulator value $A_b$, $A_g$, $A_r$ in a color channel b, g, r is calculated, for example, as the sum of the intensity values that are associated with the individual image points inside a predetermined area of the image for the relevant color channel.

The following table shows in every field together the accumulator value $A_b$ for the blue color channel, the accumulator value $A_g$ for the green color channel and the accumulator value $A_r$ for the red color channel.

| $A_b$ $A_g$ $A_r$ | STD Endoscope | PDD Endoscope | AF Endoscope |
|---|---|---|---|
| STD illumination | 728 | 497 | 227 |
| | 804 | 992 | 1070 |
| | 776 | 965 | 1064 |
| PDD illumination | 857 | 3549 | 0 |
| | 1 | 109 | 0 |
| | 0 | 0 | 0 |
| AF illumination | 1862 | 3497 | 3146 |
| | 40 | 125 | 236 |
| | 0 | 0 | 0 |

For every one of the nine possible combinations of one of the three illumination spectra with one of the three endoscopes, the ratio $(A_g+A_r)/A_b$ is formed by the sum of the accumulator value $A_g$ for the green color channel and of the accumulator value $A_r$ for the red color channel as well as from accumulator value $A_b$ for the blue color channel. These ratios are indicated in the following table.

| $(A_g + A_r)/A_b$ | STD | PDD | AF |
|---|---|---|---|
| STD illumination | 2.17 | 3.94 | 9.40 |
| PDD illumination | 0.001 | 0.031 | "∞" |
| AF illumination | 0.022 | 0.036 | 0.075 |

It can be recognized that already, with a single illumination spectrum, on the basis of the ratio $(A_g+A_r)/A_b$ it is possible to distinguish whether the optical investigation system includes a standard endoscope, a PDD endoscope or an AF endoscope. For this purpose, for instance, the test method described above is modified as follows. An image of the reference surface 72 is recorded with white light illumination of the reference surface 72 or without illumination filter 24. For each of the three color channels b, g, r, with given exposure time and gain, the image brightness or brightness of a portion of the image, rendered by an accumulator value ratio $A_b$, $A_g$, $A_r$, is recorded. The ratio $(A_g+A_r)/A_b$ is calculated from the accumulator value $A_b$, $A_g$, $A_r$. If the value of this ratio $(A_g+A_r)/A_b$ lies in the vicinity of 2, the optical investigation system includes a standard endoscope; if the quotient lies in the area of 4, a PDD endoscope; and if the quotient lies in the area of 9, an AF endoscope.

It can also be recognized on the basis of the table that by ascertaining the ratio $Q1=(A_g+A_r)/A_b$ for standard illumination and the ratio $Q2=(A_g+A_r)/A_b$ for PDD illumination and by division of the two ratiosx Q1 and Q2 so obtained, the endoscope present in the optical investigation system can likewise be identified. If the ratio Q1/Q2 of the ratios for standard illumination and for PDD illumination is about 2000, a standard endoscope is present; if the ratio Q1/Q2 of the ratios is at about 100, a PDD endoscope is present; and if the ratio Q1/Q2 of the ratios is approximately zero, an AF endoscope is present.

If the operating condition of the video camera 31 can be recorded with differentiation by color channels, that is, for example for every color channel the exposure time and/or gain assume different values and can be recorded separately, then a corresponding process can be conducted with the exposure parameters $E_b$, $E_g$, $E_r$, which are associated with the individual color channels. In the aforementioned formulas, $A_b$ is replaced in each case by $E_b$, $A_g$ by $E_g$, and $A_r$ by $E_r$.

With real endoscopic or other optical investigation systems, the values of the exposure parameters E and of the resulting ratios vary or are scattered. Nevertheless, through these and similar algebraic linking or also by logical linking of exposure parameters, observation filters and/or illumination filters can be identified.

The operating condition of a video camera 31 is determined by the white balance parameters, among other means. Variants described below of the test methods described in the foregoing are based on white balance parameters as parameters of the operating condition of the video camera.

As already mentioned, the white balance serves to produce a natural color impression. An image of a white or gray surface is recorded for the white balance. The reference surface 72 of the test apparatus 40 described above is suited for white balance if it is white or has an essentially wavelength independent remission factor in the spectral range visible to the human eye. In the white balance the signals, in particular the digital signals, are compared with one another in the three color channels. Weighting factors are calculated for the color channels so that the product of the raw signal and the weighted factor is equal for every color channel.

Instead of a weighted factor that is to be applied to the digital signal, the exposure times or gains can be modified by corresponding factors.

Because only two degrees of freedom are required in order to perform a white balance, one of the weighted factors or white balance parameters WBGb, WBGg, WBGr is not modified. According to a widely adopted convention, the white balance parameter WBGg is always WBGg=128=0x080. To compensate for an illumination with an excess blue portion, a white balance parameter WBGb<128, for example, is selected for the blue color channel. To compensate for an illumination with excess red portion, a white balance parameter WBGr<128 is selected.

With fluorescence diagnostic methods, like PDD and AF diagnostics, the white balance is used to generate an approximately natural color impression despite the employed illumination and observation filters. Because of the total transmission of the illumination filter in the blue channel, which is reduced with respect to the white light illumination, it is obvious that here white balance parameters WBGb, WBGr are selected that are clearly distinguished from the white balance parameters at white light illumination and without observation filter. Because of the differences between the illumination filters and between the observation filters for PDD and for AF diagnostics as explained above with reference to FIG. 4, the white balance parameters in these two fluorescence diagnostic methods also differ from one another. Different white balance parameters are obtained, again, in white balance of a video camera 31 in an optical investigation system with other filter combinations.

Figure 6:
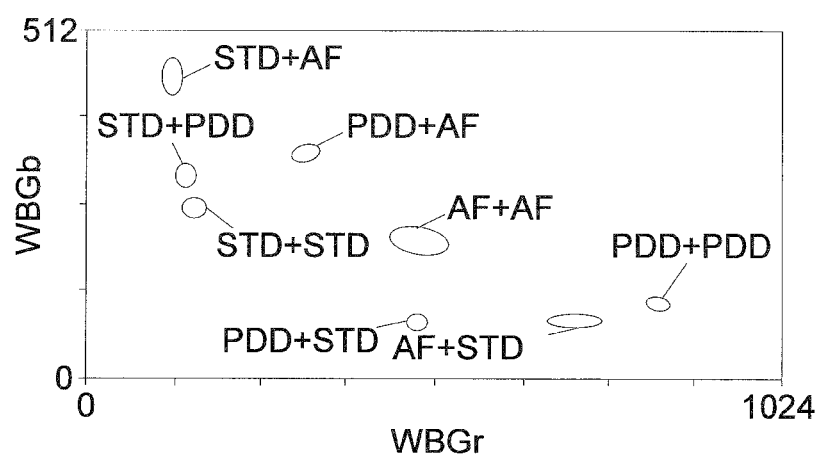
FIG. 6 shows a schematic depiction of white balance parameters.

In a schematic diagram, FIG. 6 shows typical white balance parameters after a white balance on a white, non-fluorescent reference surface with various combinations of illumination filters and observation filters. The reference surface in this example is a surface of a reference body of white PTFE. The aforementioned white balance parameter WBGr is plotted on the abscissa, the white balance parameter WBGb on the ordinate. The filter combination in each case is indicated at the measurement points, where the indication before the plus sign refers to the illumination filter and the indication after the plus sign to the observation filter. Thus "STD" means no filter (white light), "POD" means a filter for PDD and "AF" a filter for AF. Admissible filter combinations are STD+STD, PDD+PDD and AF+AF.

It can be recognized that different filter combinations have different white balance parameters as a consequence, which can be unequivocally assigned and distinguished. After conducting a white balance with an appropriate reference surface, conclusions can thus be drawn from the white balance parameter concerning the present filter combination.

Because the white balance parameters vary from camera type to camera type and in some cases even from camera to camera, the white balance parameters obtained from a white balance can, for example, be corrected by corrective parameters filed in the camera. Corrective parameters filed in the camera are, for example, white balance parameters obtained on a white surface without illumination and observation filter. These corrective parameters can be filed in the camera control device 35 instead of in the camera 31. Additional corrections can ensue for the structural form or the type of endoscope, because rigid and flexible endoscopes, endoscopes with different diameters or for different applications have different transmission spectra in the illumination beam path and in the observation beam path.

In using a non-white reference surface for a white balance, the precision or reliability of the differentiation of various filter combinations can be further improved on the basis of the white balance parameters. This is true in particular when areas of the reference surface comprise materials whose absorption or fluorescence excitation spectra have edges or flanks in the proximity of the filter edges of the illumination and observation filters that are to be differentiated.

In a schematic diagram, FIG. 7 shows white balance parameters for various filter combinations in a white balance on a reference surface made up of a covering layer of Maragloss GO 320 Fluoresco Yellow paint produced by Marabu. Abscissa and ordinate as well as designations of measured values correspond to those of FIG. 6. A comparison of FIGS. 6 and 7 shows that an especially secure identification of the existing filter combination is possible if both the white balance parameters from a white balance on a Teflon surface and the white balance parameters from a white balance on a covering layer of Marabu Maragloss GO Fluoresco 320 yellow are involved. Additional improvements are also possible, for example, by a logical or algebraic linking of the white balance parameters.

In a variant of the test method described above, after a white balance of the video camera 31 on the reference surface 72, the white balance parameters are read out or recorded as parameters of the operating condition of the video camera 31. The illumination filter 24 and the observation filter 13 are identified on the basis of the white balance parameters. The illumination filter and the observation filter can be identified even more securely if one of the two filters is already known or if the white balance is conducted successively on reference surfaces or areas of a reference surface with different optical properties.

White balance parameters—assuming linear behavior of the video camera—are independent of absolute brightness because they only describe proportions between signals in the individual color channels. Thus the white balance parameters ascertained in a white balance are also independent of the distance between the distal end 12 of the imaging device 10 and the reference surface 72. Therefore, in this variant of the test method, there is no longer a necessity for a precise positioning of the distal end 12 of the endoscope or of the imaging device in relation to the reference surface 72.

FIG. 8 shows a schematic flow diagram of a method for testing an optical investigation system, with a light source, an imaging device and a video camera for optical investigation of an object. Although the method is applicable also in optical investigation systems and test apparatuses that differ from the one presented above with reference to FIGS. 1 and 2, hereinafter for the sake of simplicity of understanding, reference numbers from FIGS. 1 and 2 are used by way of example. The method can include characteristics of the test method described above and of its described variants. In particular, the method can be a combination of several described variants.

In an optional first step 101, an expected application of the optical investigation system is recorded, for example on a user interface after a corresponding request. In an optional second step 102, a requirement associated with the expected application is ascertained on an operating condition of the video camera 31 of the optical investigation system, for example by reading out a look-up table. One or more requirements for the operating condition of the video camera 31 can alternatively be pre-established without modification.

In a third step 103, a distal end 12 of an imaging device 10, in particular of an endoscope, is inserted through an aperture 43 into a hollow space 42 in a light-insulated housing 41. In an optional fourth step 104, which can be executed immediately after the third step 103 or simultaneously with it, the distal end 12 of the imaging device 10 is positioned in a predetermined position and direction in relation to a reference surface 72 positioned in the hollow space 42. This occurs, for example, with support from a positioning device 50, which guides the imaging device 10, in particular its distal end 12, and/or holds it by form-locking or force-locking. As already mentioned above, the fourth step 104 can be omitted, for example, if ratios of exposure parameters or accumulator values are formed successively or white balance parameters are observed, because in that way the influence of the distance and of the precise positioning of the distal end 12 of the imaging device 10 relative to the reference surface can be almost eliminated.

In a fifth step 105, the reference surface 72 is illuminated with illuminating light with an illumination spectrum. If the imaging device is an endoscope 10, the illumination occurs in particular by means of the endoscope or by means of an illumination beam path in the endoscope 10. In an optional sixth step 106, a white balance is conducted, as described above, while the reference surface is illuminated. In the process, white balance parameters WBGr, WBGb, for example, are selected.

In a seventh step 107, an image is recorded by a video camera 31 during the illumination of the reference surface 72 by the imaging device 10. In an eighth step 108, the operating condition of the video camera 31 that is present during the seventh step 107 is recorded, in particular read out from the video camera 31 or the camera control device 35. Alternatively a noise level or a signal-noise distance in the recorded image, for example, is determined, from which conclusions can be drawn concerning the operating condition of the video camera 31. The operating condition of the video camera includes, for example, white balance parameters WBGr, WBGb, an exposure time valid for all color channels, a gain valid for all color channels, exposure times and gains valid for individual color channels, or accumulator values valid for individual color channels.

In an optional ninth step 109, an exposure parameter is ascertained, and in particular calculated, from the recorded operating condition of the video camera. In a tenth step 110, the ascertained exposure parameter or an algebraic or logical linking of exposure parameters or of accumulator values is compared with one or more threshold values that are associated with an expected application or apply overall to it. Alternatively or in addition, the operating condition of the video camera or the parameters that characterize it are compared with other requirements associated with the predetermined application of the optical investigation system and applying overall to it. The result of the comparison indicates the functionality or another property of the optical investigation system.

In an optional eleventh step 111, a report is issued that can include a statement on the functionality of the optical investigation system, an operating recommendation and/or an operating instruction. In a twelfth step 112, which can also be conducted at any other point in the process, patient data are recorded, for example by means of a user interface. In an optional thirteenth step 113, the patient data, the result of the test method with respect to the functionality or another property of the optical investigation system, and optionally the result of a succeeding or ongoing investigation of a patient are filed in a database by means of the optical investigation system.

In addition, model designations, series numbers, software or firmware versions and other data on components of the optical investigation system can be requested over a communication line 39 and filed in the database for documentation or logging. In addition, in the database or separately on another data carrier, the investigation of the patient can be documented or logged. Here images or a video data stream from the camera 31, for example, is filed in the database (for example in MPEG format) or on a videotape.

What is claimed is:

1. A method for testing an optical investigation system, the method comprising the steps of:
    providing an imaging device, a video camera, and a singular light source;
    providing a test apparatus, the test apparatus having a housing with an aperture at one end and being closed at the other end and including a hollow space within the housing, the test apparatus having a reference body including a reference surface with at least one predetermined optical property;
    positioning a distal end of the imaging device through the aperture and into the hollow space of the test apparatus, in such a way that the distal end of the imaging device is positionable by the test apparatus no closer than a predetermined position relative to the reference surface of the test apparatus, wherein the predetermined position corresponds to a maximum distance between the distal end of the imaging device and an observed object in an application foreseen for the optical investigation system;
    illuminating the reference surface of the test apparatus with illuminating light with a first spectrum using the singular light source alone;
    illuminating the reference surface with illuminating light with a second spectrum using the singular light source alone;
    recording the reference surface using the imaging device and video camera;
    during the recording of an image while illuminating the reference surface with illuminating light with the first spectrum, recording a first operating condition of the video camera;
    during the recording of an image while illuminating the reference surface with illuminating light with the second spectrum, recording a second operating condition of the video camera; and
    determining at least one of a functionality and a property of the optical investigation system using the first recorded operating condition and the second recorded operating condition.

2. The method of claim 1, further comprising:
    recording the expected application of the optical investigation system; and
    ascertaining a requirement associated with the expected application of the optical investigation system, so that a functionality for the expected application is present if at least one of the first operating condition and the second operating condition corresponds to the requirement.

3. The method of claim 2, wherein the reference surface is illuminated with an irradiance that equals a predetermined fraction of an irradiance applied in the expected application of the optical investigation system.

4. The method of claim 1, further comprising:
    ascertaining an indicator parameter from the recorded first operating condition and the recorded second operating condition; and
    comparing the ascertained indicator parameter with a threshold value.

5. The method of claim 1, wherein the recording of at least one of the first operating condition and the second operating condition includes at least one of: (i) ascertaining an exposure parameter for each of a number of color channels; (ii) recording a white balance parameter; and (iii) a noise level or a signal-noise distance in a recorded image.

6. The method of claim 1, further comprising:
recording patient data; and
filing information on the functionality or the other property as well as the patient data in a databank.

7. The method of claim 1, the method further comprising the step of positioning an illumination filter in an illumination beam path defined by the illumination light emitted by the singular light source.

8. The method of claim 1, the method further comprising the step of positioning an observation filter in an observation beam path defined by light reflected from the reference surface.

9. The method of claim 1, wherein the video camera is configured to record a plurality of successive images.

10. The method of claim 1, wherein the step of illuminating the reference surface of the test apparatus with illuminating light with the second spectrum is performed after the step of illuminating the reference surface of the test apparatus with illuminating light with the first spectrum.

11. The method of claim 1, wherein the reference surface is positionally-fixed relative to the housing of the test apparatus.

12. A control device for an optical investigation system, comprising:
a singular light source;
a video camera;
an imaging device, the imaging device having a distal end;
a test apparatus, the test apparatus having a housing having an aperture at one end and being closed at the other end and including a hollow space within the housing, the test apparatus having a reference body including a reference surface with at least one predetermined optical property, where the distal end of the imaging device is positionable through the aperture and into the hollow space of the test apparatus, in such a way that the distal end of the imaging device is positionable by the test apparatus no closer than a predetermined position relative to the reference surface of the test apparatus, wherein the predetermined position corresponds to a maximum distance between the distal end of the imaging device and an observed object in an application foreseen for the optical investigation system;
the singular light source alone being configured to illuminate the reference surface with illuminating light with a first spectrum and illuminate the reference surface with illuminating light with a second spectrum;
said video camera and said imaging device being configured to record said reference surface;
a memory, said memory configured to store a first recorded operating condition of said video camera during recording of an image of the reference surface while illuminating the reference surface with illuminating light with the first spectrum, and said memory configured to store a second recorded operating condition of the video camera during recording of an image of the reference surface while illuminating the reference surface with illuminating light with the second spectrum; and
a processor, said processor configured to determine at least one of a functionality and a property of the optical investigation system using the first recorded operating condition and the second recorded operating condition.

13. The method of claim 1, wherein the providing step involves guiding the distal end of the imaging device until the distal end reaches the predetermined position relative to the reference surface of the test apparatus.

14. The method of claim 1, further comprising holding the distal end of the imaging device in the predetermined position relative to the reference surface of the test apparatus.

15. The method of claim 1, wherein the providing step involves guiding the distal end of the imaging device until the distal end reaches the predetermined position relative to the reference surface of the test apparatus; and
wherein the method further comprises holding the distal end of the imaging device in the predetermined position relative to the reference surface of the test apparatus.

16. The method of claim 1, wherein in the predetermined position an optically recognizable mark on the reference surface lies at a predetermined site in an image captured by the distal end of the imaging device.

17. The control device of claim 12, wherein the reference surface is positionally-fixed relative to the housing of the test apparatus.

18. The control device of claim 12, wherein said video camera is a separate unit from the imaging device, and is optically coupled with the imaging device.

19. The control device of claim 12, wherein said video camera is integrated into the imaging device.

20. The control device of claim 12, wherein the reference surface has a spatial shape of a portion of a spherical surface or of a cylindrical mantle.

21. The control device of claim 12, wherein the imaging device is coupled to the singular light source via a cable.

22. The control device of claim 12, wherein the reference surface has an indicator area and reference area, wherein the indicator area and the reference area have respective optical properties that differ from those of the rest of the reference surface.

23. The control device of claim 12, wherein the reference surface does not have any openings.

24. The control device of claim 12, wherein the singular light source and the imaging device are discrete components of the control device, and the singular light source is coupled to the imaging device.

25. The control device of claim 12, wherein in the predetermined position an optically recognizable mark on the reference surface lies at a predetermined site in an image captured by the distal end of the imaging device.

* * * * *